United States Patent
Ishikawa et al.

(10) Patent No.: US 7,777,075 B2
(45) Date of Patent: Aug. 17, 2010

(54) FLUOROETHERCARBOXYLIC ACID AND PRODUCTION METHOD THEREOF, SURFACTANT, METHOD OF PRODUCING FLUOROPOLYMER AND AQUEOUS DISPERSION USED THEREOF

(75) Inventors: Takuji Ishikawa, Osaka (JP); Nobuhiko Tsuda, Osaka (JP); Yoshihiro Yamamoto, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/348,025

(22) Filed: Jan. 2, 2009

(65) Prior Publication Data
US 2009/0176942 A1 Jul. 9, 2009

Related U.S. Application Data

(60) Provisional application No. 61/018,829, filed on Jan. 3, 2008, provisional application No. 61/040,497, filed on Mar. 28, 2008.

(51) Int. Cl.
| | |
|---|---|
| C07C 59/135 | (2006.01) |
| C07C 51/367 | (2006.01) |
| C07C 51/31 | (2006.01) |
| C07C 51/363 | (2006.01) |
| C07C 51/47 | (2006.01) |
| B01F 17/44 | (2006.01) |
| C08F 2/24 | (2006.01) |
| C08F 14/18 | (2006.01) |
| C07B 61/00 | (2006.01) |

(52) U.S. Cl. ........................ 562/568; 562/605
(58) Field of Classification Search .................. None
See application file for complete search history.

(56) References Cited

U.S. PATENT DOCUMENTS

| 2006/0281946 A1 | 12/2006 | Morita et al. | |
| 2007/0015864 A1 | 1/2007 | Hintzer et al. | |
| 2007/0276068 A1 * | 11/2007 | Hintzer et al. | 524/284 |

FOREIGN PATENT DOCUMENTS

WO  2005003075 A1  1/2005

* cited by examiner

*Primary Examiner*—Daniel M Sullivan
*Assistant Examiner*—Yevegeny Valenrod
(74) *Attorney, Agent, or Firm*—Sughrue Mion, PLLC

(57) ABSTRACT

The invention provides a fluoroethercarboxylic acid which is represented by the general formula (I):

$$Rf^1OCHFCF_2ORf^2COOM \qquad (I)$$

wherein $Rf^1$ represents a partially or fully fluorinated alkyl group, which may optionally be interrupted with one or more oxygen atoms, $Rf^2$ represents a partially or fully fluorinated alkylene group, which may optionally be interrupted with one or more oxygen atoms, and M represents a monovalent alkali metal, $NH_4$ or H. The fluoroethercarboxylic acid can be suitably used as a surfactant and is low in bioaccumulation. The invention is also a method of fluoropolymer production and an aqueous fluoropolymer dispersion, using the fluoroethercarboxylic acid as a surfactant.

16 Claims, No Drawings

US 7,777,075 B2

FLUOROETHERCARBOXYLIC ACID AND PRODUCTION METHOD THEREOF, SURFACTANT, METHOD OF PRODUCING FLUOROPOLYMER AND AQUEOUS DISPERSION USED THEREOF

CROSS-REFFERENCE TO RELATED APPLICATIONS

This Application claims benefit under 35 U.S.C §119(e) of U.S. Provisional Application No. 61/018,829 filed Jan. 3, 2008, Provisional Application No. 61/040,497 filed Mar. 28, 2008 incorporated herein by reference in its entirety.

TECHNICAL FIELD

The present invention relates to a fluoroethercarboxylic acid and a method of producing the same, a surfactant, a method of fluoropolymer production utilizing the same as well as an aqueous dispersion.

BACKGROUND ART

Patent Document 1 describes fluoroethercarboxylic acids obtainable by allowing an alcohol to add to a perfluoro(vinyl ether) and reducing the compound obtained.

Patent Document 2 describes fluoroethercarboxylic acid salts obtainable by utilizing the ring-opening reaction of tetrafluorooxetane.

[Patent Document 1] United States Patent Application Publication 2007/0015864
[Patent Document 2] International Publication 2005/003075

DISCLOUSRE OF INVENTION

Problems Which the Invention is to Solve

It is an object of the present invention to provide a novel compound which can be suitably used as a surfactant and is low in bioaccumulation as well as a method of fluoropolymer production using the novel compound, a surfactant and an aqueous fluoropolymer dispersion. The novel compound of the invention shows higher surfactant activity and is lower in bioaccumulation as compared with a conventional fluoroethercarboxylic acid.

Means for Solving the Problems

The invention is a fluoroethercarboxylic acid which is represented by the general formula (I):

Rf$^1$OCHFCF$_2$ORf$^2$COOM    (I)

wherein Rf$^1$ represents a partially or fully fluorinated alkyl group, which may optionally be interrupted with one or more oxygen atoms, Rf$^2$ represents a partially or fully fluorinated alkylene group, which may optionally be interrupted with one or more oxygen atoms, and M represents a monovalent alkali metal, NH$_4$ or H.

The invention is a production method of the fluoroethercarboxylic acid mentioned above, which comprises the addition reaction step of allowing a hydroxyalkanoic acid derivative represented by the general formula (1):

HOCH$_2$CF$_2$COOR    (1)

wherein R represents an alkyl group or H, to add to a fluoro(vinyl ether) represented by the general formula (2):

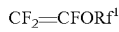

CF$_2$=CFORf$^1$    (2)

wherein Rf$^1$ is as defined above, in the presence of an alkali compound.

The invention is a production method of a fluoroethercarboxylic acid which comprises the step of bringing the fluoroethercarboxylic acid mentioned above into contact with fluorine to give the fluoroethercarboxylic acid represented by the general formula (II):

Rf$^1$OCF$_2$CF$_2$ORf$^2$COOM    (II)

wherein Rf$^1$ represents a partially or fully fluorinated alkyl group, which may optionally be interrupted with one or more oxygen atoms, Rf$^2$ represents a partially or fully fluorinated alkylene group, which may optionally be interrupted with one or more oxygen atoms, and M represents a monovalent alkali metal, NH$_4$ or H.

The invention is a surfactant comprising the fluoroethercarboxylic acid mentioned above.

The invention is a surfactant for use in polymerization processes which comprises the fluoroethercarboxylic acid mentioned above.

The invention is a production method of the fluoropolymer, which comprises the step of polymerizing a fluorine-containing monomer or monomers in an aqueous medium containing the fluoroethercarboxylic acid mentioned above.

The invention is an aqueous fluoropolymer-containing dispersion containing the fluoroethercarboxylic acid mentioned above, wherein the fluoropolymer has an average particle diameter of 50 to 500 nm.

The invention is a production method of purified aqueous dispersion, which comprises the step (A) of bringing the aqueous dispersion mentioned above into contact with an anion exchange resin in the presence of a nonionic surfactant and the step (B) of concentrating the aqueous dispersion obtained in the step (A) to produce an aqueous dispersion having a solid matter content of 30 to 70% by mass of the aqueous dispersion.

The invention is a fine powder being produced by coagulating the aqueous dispersion mentioned above.

The invention is a production method of a regenerated fluoroethercarboxylic acid, which comprises the step of recovering a fluoroethercarboxylic acid represented by the general formula (I):

Rf$^1$OCHFCF$_2$ORf$^2$COOM    (I)

wherein Rf$^1$, Rf$^2$ and M are as defined above from at least one source selected from among a wastewater generated in the step of coagulation of the aqueous dispersion mentioned above, a wastewater generated upon washing thereof and/or a off-gas generated in drying thereof, and the step of purifying the recovered fluoroethercarboxylic acid obtained by the step to produce the regenerated fluoroethercarboxylic acid.

In the following, the invention is described in detail.

The fluoroethercarboxylic acid of the invention is a novel compound represented by the general formula (I):

Rf$^1$OCHFCF$_2$ORf$^2$COOM    (I)

wherein Rf$^1$ represents a partially or fully fluorinated alkyl group, which may optionally be interrupted with one or more oxygen atoms, Rf$^2$ represents a partially or fully fluorinated alkylene group, which may optionally be interrupted with one or more oxygen atoms, and M represents a monovalent alkali metal, NH$_4$ or H.

The present inventors found that a fluoroethercarboxylic acid having a structure Rf$^1$OCHFCF$_2$ORf$^2$COOM, in spite of their containing at least one hydrogen atom in the structure thereof, are useful in a emulsion polymerization of a fluoroolefin and, further, that they can be separated and recovered with ease from the polymer after polymerization, and have now completed the present invention.

Thus, the fluoroethercarboxylic acid of the invention, when used as an emulsifier in a emulsion polymerization of a fluoroolefin, shows excellent surface activity and can give a high-molecular-weight fluoropolymer in a stable manner and, further, can easily separated and recovered from the polymer when a conventional method of washing is carried out after polymerization.

Furthermore, the fluoroethercarboxylic acid of the invention has a very beneficial effect, namely it is low in bioaccumulation. In the case of surfactants whose hydrophobic moiety is a fluoroalkyl group, their bioaccumulation generally tends to be low when the number of carbon atoms is small and tends to be high when the number of carbon atoms is large. Conversely, the surface activity is low when the number of carbon atoms is small and tends to be high when the number of carbon atoms is large.

Contrary to such common sense in the art, the fluoroethercarboxylic acid of the invention is low in bioaccumulation in spite of the high surface activity level thereof. The reason is presumably such that the occurrence of a partially hydrogen atom-containing specific structural moiety in the structure makes it difficult for the compound to be taken up into a living body or makes it easy for the compound, if taken up, to be excreted rapidly.

The symbol $Rf^1$ in the above general formula (I) represents a partially or fully fluorinated alkyl group, which may optionally be interrupted with one or more oxygen atoms. A preferred lower limit to the number of carbon atoms in the moiety $Rf^1$ is 1, and a preferred upper limit thereto is 3. The alkyl group is an alkyl group resulting from substitution of a part or the whole of the carbon atom-bound hydrogen atom by fluorine atom.

The alkyl group mentioned above may contain 1 to 5 oxygen atoms in the main chain thereof. A preferred upper limit to the number of oxygen atoms in the above moiety $Rf^1$ is 3. The number of oxygen atoms in $Rf^1$ is preferably 0 (zero). The oxygen atom which may be contained in the above-mentioned alkylene group are ether bond-forming ones.

As the above moiety $Rf^1$, there may be mentioned $CF_3$—, $CF_3CF_2$—, $CF_3CF_2CF_2$—, $(CF_3)_2CF$—, $CF_3CF_2CF_2CF_2$—, $CF_3CF_2CF_2OCF(CF_3)CF_2$—, $HCF_2CF_2CF_2$—, $CF_3OCF(CF_3)CF_2$— and the like. Preferred among these are the groups of the formula $CF_3(CF_2)_n$— (in which n represents an integer of 0 to 2).

The symbol $Rf^2$ in the above general formula (I) represents a partially or fully fluorinated alkylene group, which may optionally be interrupted with one or more oxygen atoms. A preferred lower limit to the number of carbon atoms in the moiety $Rf^2$ is 1, and a preferred upper limit thereto is 3.

The above-mentioned alkylene group may contain 1 to 5 oxygen atoms in the main chain thereof. A preferred upper limit to the number of oxygen atoms in the above-mentioned $Rf^2$ is 3. The number of oxygen atoms in $Rf^2$ is preferably 0 (zero).

As the above moiety $Rf^2$, there may be mentioned —$CH_2CF_2$—, —$CFHCF_2$—, —$CF_2CF_2$—, —$CF_2CF_2CF_2$—, —$C(CF_3)_2$—, —$CF_2OCF_2$— and the like. Preferred among them is —$CH_2CF_2$—.

From the viewpoint of high surface activity level and good biodegradability, it is preferred that the total number of carbon atoms in $Rf^1$ and $Rf^2$ be equal to 3 to 5 or, in other words, the total number of carbon atoms in the fluoroethercarboxylic acid as a whole be equal to 6 to 8.

The symbol M in the above general formula (I) represents a monovalent alkali metal, $NH_4$ or H. As the monovalent alkali metal, there may be mentioned Li, Na, K, etc. $NH_4$ is preferred as the above M from a viewpoint of easy removability by heating treatment.

As the fluoroethercarboxylic acid of the invention, there may be mentioned, for example, $CF_3OCHFCF_2OCH_2CF_2COONH_4$, $CF_3CF_2OCHFCF_2OCH_2CF_2COONH_4$, $CF_3CF_2CF_2OCHFCF_2OCH_2CF_2COONH_4$ and the like.

The fluoroethercarboxylic acid of the invention can be produced, for example, by a production method which comprises a step of allowing a hydroxyalkanoic acid derivative represented by the general formula (1):

$$HOCH_2CF_2COOR \qquad (1)$$

wherein R represents an alkyl group or H, to add to a fluoro (vinyl ether) represented by the general formula (2):

$$CF_2\!=\!CFORf^1 \qquad (2)$$

wherein $Rf^1$ is as defined above, in the presence of an alkali compound.

The above production method can produce the fluoroethercarboxylic acid of the invention only via the step of allowing the hydroxyalkanoic acid derivative to add to the fluoro(vinyl ether) without needing any complicated production step. Furthermore, the reaction can be completed only with a catalytic amount of the alkali compound with advantage.

As for a usage of the alkali compound, there is no particular restriction but, from the reaction rate, economic efficiency and other points of view, the usage is preferably about 0.01 to 2 moles, more preferably about 0.05 to 0.6 mole, per mole of the hydroxyalkanoic acid derivative.

The alkali compound mentioned above is preferably an alcoholate, which allows the addition reaction to proceed smoothly. The alcoholate is represented by $R^1$—$OM^1$ (in which $R^1$ represents an alkyl group and $M^1$ represents a monovalent alkali metal) and includes sodium methoxide, sodium ethoxide, potassium tert-butoxide and the like. Such alkali compounds as potassium hydroxide and sodium carbonate may fail to allow the addition reaction to proceed smoothly.

The above-mentioned step of allowing the hydroxyalkanoic acid derivative to add to the fluoro(vinyl ether) is more preferably carried out in the simultaneous presence of both the alcoholate and the alcohol corresponding to the alcoholate. The alcohol corresponding to the alcoholate is, for example, tert-butanol when the alcoholate is potassium tert-butoxide.

The alcohol to be used simultaneously or the alcoholate to be used as the alkali compound is preferably a secondary alcohol or an alcoholate thereof, more preferably a tertiary alcohol or an alcoholate thereof. A tertiary alcohol-derived alcoholate, in particular, is sterically bulky in the vicinity of the hydroxyl group and therefore hardly causes significant formation of a adduct thereof with the fluoro(vinyl ether), and potassium tert-butoxide is preferably used in view of its ready availability. Similarly, a tertiary alcohol is preferably employed as the alcohol to be used simultaneously since alcoholates derived from the alcohol used simultaneously also form the corresponding adducts with the fluoro(vinyl ether).

Preferred as the secondary alcohol or tertiary alcohol from the ready availability, marked effect and selective desired compound formation points of view are isopropanol, 3-pentanol, 3-methyl-3-pentanol, 3-ethyl-3-pentanol, tert-butanol, trityl alcohol and 1,1,1,3,3,3-hexafluoro-2-propanol, among others; particularly preferred are tert-butanol and 1,1,1,3,3,3-hexafluoro-2-propanol, among others.

Such secondary alcohols and tertiary alcohols may be used either singly or in the form of a mixture of two or more of them.

As for the usage of the secondary alcohol or tertiary alcohol, there is no particular restriction but, from the reaction rate and economic efficiency points of view, the usage is preferably about 0.001 to 2 moles, more preferably about 0.01 to 0.8 mole, per mole of the raw material hydroxyalkanoic acid derivative.

As the fluoro(vinyl ether) represented by the general formula (2), there may be mentioned perfluoro(methyl vinyl ether), perfluoro(ethyl vinyl ether), perfluoro(propyl vinyl ether) and the like.

As for a specific procedure for carrying out a production method according to the invention, there is no particular restriction but a following production procedure may be mentioned.

First, an autoclave or a like pressure-resistant reaction apparatus is charged with the hydroxyalkanoic acid derivative, alkali compound and alcohol and, after substitution of the apparatus inside atmosphere with an inert gas, the apparatus inside pressure is reduced to a level lower by about 0.01 to 0.09 MPa than atmospheric pressure. On that occasion, the reaction apparatus may be cooled with an appropriate coolant to prevent the raw material losses due to the pressure reduction.

Then, the temperature of the reaction apparatus after pressure reduction is raised and, while a predetermined temperature is maintained, the fluoro(vinyl ether) in the form of a gas or liquid is introduced into the apparatus. The reaction temperature may be varied according to the rate of the reaction between the raw materials; when the rate of reaction and the selectivity of the reaction are taken into consideration, the reaction temperature is generally set at about 0 to 200° C., preferably about 20 to 100° C.

As a method of introducing the fluoro (vinyl ether) there may be mentioned a method comprising introducing the whole amount thereof into the apparatus at the time of starting the reaction and, further, a method comprising carrying out the introduction continuously or intermittently, for example a method comprising maintaining a rate of introduction at a constant level or a method comprising maintaining the introduction pressure at a constant level. In particular, the method comprising maintaining the introduction pressure at a constant level is preferred as a method capable of making the best of a simplicity of apparatus and procedure and the reaction time-reducing effect. The pressure to be employed on that occasion is not particularly restricted but, when the rate of reaction and a inhibition of polymerization of the fluoro (vinyl ether) are taken into consideration, a pressure of about 0.1 to 3 MPa is preferred.

More preferably, the above production method comprises a step of preparing a hydroxyalkanoic acid derivative represented by the general formula (1) by causing a ring opening of tetrafluorooxetane. When it includes the step utilizing the oxetane ring opening reaction, the production method can very easily give a fluoroethercarboxylic acid of the invention which has —OCHFCF$_2$O— structure and in which Rf$^2$ is —CH$_2$CF$_2$—.

The ring opening of tetrafluorooxetane can be realized by heating tetrafluorooxetane in an alcohol containing an alkali compound. As the alkali compound to be used in the ring opening reaction, there may be mentioned sodium hydroxide, potassium hydroxide, sodium acetate, potassium carbonate and the like.

The alcohol to be used in the ring opening reaction is represented by R—OH (in which R is as defined above) and the terminal alkyl group R in the hydroxyalkanoic acid derivative represented by the general formula (1) is derived from the alkyl group of the alcohol used. As the group R, there may be mentioned methyl, ethyl and propyl, among others.

The above-mentioned ring opening reaction of tetrafluorooxetane can be carried out generally under such conditions as a temperature of 0 to 200° C. and a pressure of 0 to 3 MPa.

The fluoroethercarboxylic acid of the invention can also be produced by a production method comprising a step of allowing a hydroxycarboxylic acid represented by the general formula (3):

$$(CF_3)_2C(OH)COOM \qquad (3)$$

wherein M is as defined above, to add to a fluoro(vinyl ether) represented by the general formula (2) in the presence of an alkali compound.

The addition of a hydroxycarboxylic acid represented by the general formula (3) can readily give a fluoroethercarboxylic acid which has a —OCHFCF$_2$O— structure and in which Rf$^2$ is —C(CF$_3$)$_2$—.

The hydroxycarboxylic acid represented by the general formula (3) can be produced by oxidizing (CF$_3$)$_2$C=CFOCH$_3$ with a ruthenium compound or an osmium compound to give (CF$_3$)$_2$C(OH)COOCH$_3$, followed by hydrolysis of this ester in a conventional manner.

In each production method mentioned above, the compound obtained by the addition reaction may be further subjected to alkali hydrolysis, followed by neutralization with an acid, if desired further followed by neutralization with aqueous ammonia.

The production method of a fluoroethercarboxylic acid, which comprises the step of the fluoroethercarboxylic acid of the invention is brought into contact with fluorine to give a fluoroethercarboxylic acid represented by the general formula (II):

$$Rf^1OCF_2CF_2ORf^2COOM \qquad (II)$$

wherein Rf$^1$, Rf$^2$ and M are as defined above, also constitutes an aspect of the present invention.

The fluoroethercarboxylic acid of the invention can be suitably used as a surfactant. A surfactant comprising the fluoroethercarboxylic acid mentioned above also constitutes an aspect of the present invention. The surfactant of the invention which contains at least one fluoroethercarboxylic acid represented by the general formula (I) or (II) given hereinabove can be used as a surfactant, and the surfactant may contain two or more fluoroethercarboxylic acid species.

The surfactant of the invention, which comprises the fluoroethercarboxylic acid or acids mentioned above, can show an adequate level of surface activity in various fields of application. The surfactant of the invention can be used in such a field of application as fluoropolymer production.

The surfactant of the invention is preferably used in the form of a salt from a water solubility viewpoint, more preferably in the form of an ammonium salt since this shows little tendency to remain in the product resins.

The surfactant of the invention is also preferably used in its carboxylic acid form. In this case, a acid form shows improved surface activity in water as compared with a salt form; for example, at the same molar concentration level, the acid form brings about lower surface tension and, as a result, when used in polymerization, it gives the following advantages, among others: more stable and small polymer particles are obtained, the polymer colloid obtained is highly stable, and agglomerates are hardly formed, hence the polymerization can be continued until a high polymer concentration is attained.

The present invention is also a method of the fluoropolymer production, wherein a fluoromonomer is or fluoromonomers are polymerized in an aqueous medium containing the above-described fluoroethercarboxylic acid.

The method of fluoropolymer production according to the invention can produce a fluoropolymer efficiently as a result of using at least one fluoroethercarboxylic acid species as specified above as a surfactant. In carrying out the fluoropolymer production method of the invention, two or more fluoroethercarboxylic acids as defined above may be used simultaneously as surfactants, and a surfactant-active compound other than the above-mentioned fluoroethercarboxylic acid may be used simultaneously, if it is volatile or is allowed to remain in a fluoropolymer-based molding or the like. Use may be made, as the other surfactant-active compound, of any of those mentioned hereinabove.

Further, in carrying out the fluoropolymer production method of the invention, an additive or additives may be used, in addition to the above-mentioned fluoroethercarboxylic acid, if desired together with some other compound having surface activity, to stabilize each compound. Usable as the additive may be any of those enumerated hereinabove.

In carrying out the fluoropolymer production method of the invention, the polymerization is carried out by charging a polymerization reaction vessel with an aqueous medium, the above-mentioned fluoroethercarboxylic acid and a monomer or monomers, if necessary together with some other additive or additives, stirring the reaction vessel contents, maintaining the reaction vessel at a predetermined polymerization temperature and then adding a predetermined amount of a polymerization initiator to initiate the polymerization reaction. After the start of the polymerization reaction, the monomer or monomers, the polymerization initiator, a chain transfer agent and/or the above-mentioned fluoroethercarboxylic acid, for instance, may be supplemented according to an intended purpose. In the above-mentioned polymerization, the polymerization temperature is generally 5 to 120° C. and the polymerization pressure is generally 0.05 to 10 MPaG. The polymerization temperature and pressure are to be properly selected according to the monomer species employed, the desired molecular weight of the fluoropolymer and the rate of reaction.

In carrying out the fluoropolymer production method of the invention, the pH at the time of the start of the polymerization is preferably adjusted, for example, to 6 or below, preferably 5 or below, more preferably 4 or below, still more preferably 3 or below, so that a more stable polymer colloid may be obtained.

The above-mentioned fluoroethercarboxylic acid or acids are added preferably at a total addition level of 0.0001 to 10% by mass relative to 100% by mass of the aqueous medium. A more preferred lower limit is 0.001% by mass, and a more preferred upper limit is 1% by mass. At levels below 0.0001% by mass, the dispersibility may possibly become insufficient and, at levels exceeding 10% by mass, no more additional effect corresponding to the addition level will be obtained and, rather, the rate of polymerization may possibly be reduced or the reaction may be terminated. The level of addition of the compound(s) mentioned above is to be properly selected according to the monomer species employed and the desired molecular weight of the fluoropolymer, among others.

The polymerization initiator is not particularly restricted but may be any one capable of generating radicals within the polymerization temperature range mentioned above; thus, any of a known oil-soluble and/or water-soluble polymerization initiator can be used. Further, the polymerization may be initiated by using a reducing agent or the like in combination to form a redox system. A concentration of the polymerization initiator is to be properly selected according to the monomer species, the desired molecular weight of the fluoropolymer and the rate of reaction.

The aqueous medium mentioned above is a reaction medium for allowing the polymerization to proceed and means a water-containing liquid. The aqueous medium is not particularly restricted but may be any one provided that it contains water; for example, it may be one comprising water and, for example, a fluorine-free organic solvent such as an alcohol, ether or ketone and/or a fluorinated organic solvent having a boiling point of not higher than 40° C. Thus, in a case of suspension polymerization, for instance, such a fluorinated organic solvent as C318 may be used.

In the above-mentioned polymerization, it is further possible to adjust the rate of polymerization and the molecular weight by adding any of a known chain transfer agent and a radical scavenger according to the intended purpose.

The fluoropolymer production method of the invention may also comprise a step of obtaining an aqueous emulsion (seed dispersion) by emulsion polymerization of a monomer or monomers in an aqueous medium in the presence of the fluoroethercarboxylic acid mentioned above and a step of subjecting a monomer or monomers to emulsion polymerization (seed polymerization) in the presence of the above-mentioned aqueous emulsion (seed dispersion).

The fluoropolymer mentioned above is a polymer obtained by polymerizing a fluoromonomer or fluoromonomers and, according to an intended purpose, it may also be a polymer resulting from copolymerization of a fluorine-free monomer or monomers.

As the above-mentioned fluoromonomer, there may be mentioned, among others, fluoroolefins, preferably fluoroolefins containing 2 to 10 carbon atoms; a fluorinated cyclic monomers; and fluorinated alkyl vinyl ethers represented by the formula $CY_2=CYOR$ or $CY_2=CYOR^2OR^3$ (in which Y is H or F, R and $R^3$ each is a fluorine alkyl group containing 1 to 8 carbon atoms as resulting from substitution of part or all of the hydrogen atoms by fluorine atom and $R^2$ is a fluorinated alkylene group containing 1 to 8 carbon atoms as resulting from substitution of part or all of the hydrogen atoms by fluorine atom).

The fluoroolefins preferably contain 2 to 6 carbon atoms. As the fluoroolefins containing 2 to 6 carbon atoms, there may be mentioned, for example, tetrafluoroethylene [TFE], hexafluoropropylene [HFP], chlorotrifluoroethylene [CTFE], vinyl fluoride, vinylidene fluoride [VDF], trifluoroethylene, hexafluoroisobutylene and perfluorobutylethylene. As preferred examples of the fluorinated cyclic monomers, there may be mentioned perfluoro-2,2-dimethyl-1,3-dioxole [PDD] and perfluoro-2-methylene-4-methyl-1,3-dioxolane [PMD].

Referring to the fluorinated alkyl vinyl ethers, the moieties R and $R^3$ each preferably contains 1 to 4 carbon atoms and more preferably is an alkyl group with all the hydrogen atoms substituted by fluorine atom, and the moiety $R^2$ preferably contains 2 to 4 carbon atoms and more preferably is an alkylene group with all the hydrogen atoms substituted by fluorine atom.

As the fluorine-free monomers mentioned above, there may be mentioned hydrocarbon-based monomers reactive with the fluorine-containing monomers mentioned above. The hydrocarbon-based monomers include, among others, alkenes such as ethylene, propylene, butylenes and isobutylene; alkyl vinyl ethers such as ethyl vinyl ether, propyl vinyl ether, butyl vinyl ether, isobutyl vinyl ether and cyclohexyl vinyl ether; vinyl esters such as vinyl acetate, vinyl propionate, vinyl n-butyrate, vinyl isobutyrate, vinyl valerate, vinyl pivalate, vinyl caproate, vinyl caprylate, vinyl caprate, vinyl versatate, vinyl laurate, vinyl myristate, vinyl palmitate, vinyl stearate, vinyl benzoate, vinyl p-tert-butylbenzoate, vinyl cyclohexanecarboxylate, vinyl monochloroacetate, vinyl adipate, vinyl acrylate, vinyl methacrylate, vinyl crotonate, vinyl sorbate, vinyl cinnamate, vinyl undecylenate, vinyl hydroxyacetate, vinyl hydroxypropionate, vinyl hydroxybutyrate, vinyl hydroxyvalerate, vinyl hydroxyisobutyrate and vinyl hydroxycyclohexanecarboxylate; alkyl allyl ethers such as ethyl allyl ether, propyl allyl ether, butyl allyl ether, isobutyl allyl ether and cyclohexyl allyl ether; and alkyl allyl esters such as allyl acetate, allyl propionate, allyl butyrate, allyl isobutyrate and allyl cyclohexanecarboxylate.

The fluorine-free monomers further include functional group-containing hydrocarbon-based monomers. As the functional group-containing hydrocarbon-based monomers, there may be mentioned, for example, hydroxyalkyl vinyl ethers such as hydroxyethyl vinyl ether, hydroxypropyl vinyl ether, hydroxybutyl vinyl ether, hydroxyisobutyl vinyl ether and hydroxycyclohexyl vinyl ether; carboxyl group-containing, fluorine-free monomers such as itaconic acid, succinic acid, succinic anhydride, fumaric acid, fumaric anhydride, crotonic acid, maleic acid, maleic anhydride and perfluorobutenoic acid; glycidyl group-containing, fluorine-free monomers such as glycidyl vinyl ether and glycidyl allyl ether; amino group-containing, fluorine-free monomers such as aminoalkyl vinyl ethers and aminoalkyl allyl ethers; amide group-containing, fluorine-free monomers such as (meth)acrylamide and methylolacrylamide.

such a fluoropolymer suitably producible by the fluoropolymer production method of the invention, there may be mentioned TFE polymers in which the monomer accounting for the highest monomer mole fraction in the polymer (hereinafter "most abundant monomer") is TFE, VDF polymers in which the most abundant monomer is VDF, and CTFE polymers in which the most abundant monomer is CTFE.

The TFE polymers may suitably be a TFE homopolymer, or copolymers derived from (1) TFE, (2) one or more fluorine-containing monomers other than TFE, which contain 2 to 8 carbon atoms, in particular HFP and/or CTFE, and (3) another monomer or other monomers. As the other monomers mentioned above under (3), there may be mentioned, for example, fluoro(alkyl vinyl ether) species having an alkyl group containing 1 to 5 carbon atoms, in particular 1 to 3 carbon atoms; fluorodioxole; perfluoroalkylethylenes; ω-hydroperfluoroolefins, etc.

Suitable examples of the VDF polymers are, among others, VDF homopolymers [PVDF], and copolymers composed of (1) VDF and (2) one or more fluoroolefins other than VDF, which contain 2 to 8 carbon atoms, in particular TFE, HFP and/or CTFE, and (3) perfluoro(alkyl vinyl ether) species having an alkyl group containing 1 to 5 carbon atoms, in particular 1 to 3 carbon atoms.

The CTFE polymers may suitably be a CTFE homopolymer, or copolymers composed of (1) CTFE, (2) one or more fluoroolefins other than CTFE, which contain 2 to 8 carbon atoms, and (3) one or more perfluoro(alkyl vinyl ether) species having an alkyl group containing 1 to 5 carbon atoms, in particular 1 to 3 carbon atoms.

The CTFE polymers may further be copolymers of CTFE and one or more fluorine-free monomers and, as the fluorine-free monomers, there may be mentioned alkenes such as ethylene and propylene; vinyl esters; and vinyl ethers, among others.

A fluoropolymer produced by the fluoropolymer production method of the invention may be glassy, plastic or elastomeric. These forms are noncrystalline or partially crystalline and can be subjected to compression sintering processing, melt processing or non-melt processing.

In accordance with the production method for the fluoropolymer of the invention, there can suitably be produced, for example, (I) tetrafluoroethylene polymers [TFE polymers] as non-melt processible resins, (II) ethylene/TFE copolymers [ETFE], TFE/HFP copolymers [FEP] and TFE/perfluoro(alkyl vinyl ether) copolymers [PFA, MFA, etc.] as melt-processible resins, and (III) such elastomeric copolymers as TFE/propylene copolymers, TFE/propylene/third monomer copolymers (the third monomer being VDF, HFP, CTFE, perfluoro(alkyl vinyl ether) and/or the like), TFE/perfluoro(alkyl vinyl ether) copolymers; HFP/ethylene copolymers, HFP/ethylene/TFE copolymers; PVDF; VDF/HFP copolymers, HFP/ethylene copolymers, VDF/TFE/HFP copolymers and like thermoplastic elastomers; and fluorine-containing segmented polymers described in Japanese Patent Publication S61-49327.

The perfluoro(alkyl vinyl ether) mentioned above is represented by the formula:

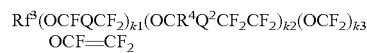
$$Rf^3(OCFQCF_2)_{k1}(OCR^4Q^2CF_2CF_2)_{k2}(OCF_2)_{k3}$$
$$OCF{=}CF_2$$

wherein $Rf^3$ represents a perfluoroalkyl group containing 1 to 6 carbon atoms, k1, k2 and k3 may be the same or different and each is an integer of 0 to 5 and Q, $Q^2$ and $R^4$ are the same or different and each is F or $CF_3$.

The fluoropolymer mentioned above may have a core-shell structure. As the fluoropolymer having a core-shell structure, there may be mentioned, for example, modified PTFE species in which each particle is comprised of a high-molecular-weight PTFE core and a lower-molecular-weight PTFE or modified PTFE shell. As such modified PTFE species, there may be mentioned, for example, PTFE species described in Japanese Kohyo (laid open under PCT) Publication 2005-527652.

The above-mentioned non-melt processible resins (I), melt-processible resins (II) and elastomeric polymers (III), which are suitably producible by the fluoropolymer production method of the invention are preferably produced in the following manner.

(I) Non-Melt Processible Resin

In carrying out the production method for the fluoropolymer of the invention, the polymerization for producing a TFE polymer is generally carried out at a polymerization temperature of 10 to 100° C. and a polymerization pressure of 0.05 to 5 MPa.

In the above polymerization, a pressure-resistant reaction vessel equipped with a stirrer is charged with pure water and the fluoroethercarboxylic acid of the invention and, after deoxygenation, further charged with TFE, the temperature is raised to a predetermined level, and a polymerization initiator is added to initiate the reaction. Since otherwise the pressure lowers with the progress of the reaction, an additional quantity of TFE is fed to the reaction vessel continuously or intermittently so as to maintain the initial pressure. After completion of feeding of a predetermined amount of TFE, the feeding is stopped, the TFE remaining in the reaction vessel is purged, and the temperature is returned to room temperature. The reaction is thus finished.

In the TFE polymer production mentioned above, one or more of the various modifier monomers known in the art may be used concomitantly. In the present specification, the term "tetrafluoroethylene polymer [TFE polymer]" conceptually includes not only TFE homopolymers but also those copolymers of TFE and a modifier monomer(s) which are non-melt-processable (hereinafter referred to as "modified PTFEs").

As the modifier monomers, there may be mentioned, among others, perhaloolefins such as HFP and CTFE; fluoro (alkyl vinyl ether) species having an alkyl group containing 1 to 5, in particular 1 to 3, carbon atoms; fluorinated cyclic monomers such as fluorodioxole; perhaloalkylethylenes; and ω-hydroperhaloolefins. The modifier monomer feeding may be carried out initially all at once, or continuously, or intermittently in portions, according to the intended purpose and the feeding of TFE.

The modifier monomer content in the modified PTFEs is generally within the range of 0.001 to 2 mole percent.

In producing the TFE polymer, the above-mentioned fluoroethercarboxylic acid can be used within the range of usage in the method of producing the fluoropolymer according to the invention. Generally, they are used at an addition level of 0.0001 to 2% by mass relative to the aqueous medium. The fluoroethercarboxylic acid concentration is not particularly restricted provided that it is within the above range but the addition is generally carried out at the time of start of the polymerization at a level not higher than the critical micelle concentration (CMC). When the addition level is excessively high, acicular particles with a large aspect ratio are formed, hence the aqueous dispersion becomes gel-like and the stability is impaired.

In producing the TFE polymer, persulfate salts (e.g. ammonium persulfate) or organic peroxides such as disuccinoyl peroxide and diglutaroyl peroxide may be used as the polymerization initiator, either singly or in the form of a mixture of these. These may also be used in combination with a reducing agent such as sodium sulfite to give redox systems. Further, during polymerization, the radical concentration in the system can be adjusted by adding a radical scavenger such as hydroquinone or catechol or a peroxide-decomposing agent such as ammonium sulfite.

In producing the TFE polymer, use can be made of any of the known chain transfer agents, for example saturated hydrocarbons such as methane, ethane, propane and butane, halogenated hydrocarbons such as chloromethane, dichloromethane and difluoromethane, alcohols such as methanol and ethanol, and hydrogen. Those which are gaseous at ordinary temperature and ordinary pressure are preferred.

The chain transfer agent is generally used in an amount of 1 to 1000 ppm, preferably 1 to 500 ppm, relative to the total feed of TFE.

In producing the TFE polymer, use can further be made, as a dispersion stabilizer for the reaction system, of 2 to 10 parts by mass, per 100 parts by mass of the aqueous medium, of a saturated hydrocarbon which contains not less than 12 carbon atoms, is substantially inert to the reaction and occurs as a liquid under the reaction conditions mentioned above. Furthermore, ammonium carbonate, ammonium phosphate or the like may be added as a buffering agent for adjusting the pH during reaction.

At the time when the above-mentioned TFE polymer polymerization is complete, an aqueous dispersion with a solid matter concentration of 30 to 70% by mass and an average particle diameter of 50 to 500 nm can be obtained. Such aqueous dispersion containing the above-mentioned fluoroethercarboxylic acid and the fluoropolymer in which the fluoropolymer has an average particle diameter of 50 to 500 nm also constitutes an aspect of the present invention. Further, by using the above-mentioned fluoroethercarboxylic acid, it is possible to obtain an aqueous dispersion containing TFE polymer particles having a small particle diameter not greater than 0.3 μm. At the time of completion of the above-mentioned polymerization, the TFE polymer has a number average molecular weight of 1,000 to 10,000,000.

The above-mentioned aqueous TFE polymer dispersion can be used, after coagulation, washing and drying, in the form of a fine powder in various fields of application. Such fine powder produced by coagulation of the above-mentioned aqueous dispersion also constitutes an aspect of the present invention. In subjecting the aqueous TFE polymer dispersion to coagulation, the aqueous dispersion obtained by emulsion polymerization, for example a polymer latex, is generally diluted to a polymer concentration of 10 to 20% by mass using water and, after pH adjustment to a neutral or alkaline level under certain circumstances, stirred, in a vessel equipped with a stirrer, more vigorously than the stirring during reaction. The coagulation may also be carried out by stirring while adding, as a coagulating agent, a water-soluble organic compound such as methanol or acetone, an inorganic salt such as potassium nitrate or ammonium carbonate or an inorganic acid such as hydrochloric acid, sulfuric acid or nitric acid or the like. The coagulation may also be carried out continuously using an in-line mixer or the like.

When one or more of pigments for coloration and/or one or more of various fillers for improvements in mechanical properties are added before or during the coagulation mentioned above, it is possible to obtain a pigment- and/or filler-containing TFE polymer fine powder containing the pigment(s) and/or filler(s) uniformly mixed therein.

The drying of the wet powder obtained by coagulation of the aqueous TFE polymer dispersion is generally effected using such techniques as vacuum, high-frequency or hot air while maintaining the wet powder in a condition such that it flows little, preferably it stands still. Friction among powder particles at elevated temperatures, in particular, generally exerts unfavorable influences on the TFE polymer in fine powder form. This is because this kind of the particles comprising TFE polymer have a property such that they readily fibrillate upon exposure to even a weak shearing force and lose their original stable particle structure.

The above drying is carried out at a drying temperature of 10 to 250° C., preferably 100 to 200° C.

The TFE polymer fine powder thus obtained is preferably used for molding and, as proper uses thereof, there may be mentioned, among others, tubes for use in hydraulic or fuel systems in airplanes or automobiles, and, further, flexible hoses for transporting liquid chemicals, steam or the like, and electric wire coatings or coverings.

The aqueous TFE polymer dispersion obtained by the above-mentioned polymerization, when supplemented with a nonionic surfactant, is stabilized and, after further concentration, is preferably used in various fields of application in the form of a composition supplemented with an organic or inorganic filler(s) according to the intended purpose. The above composition, when applied to metal or ceramic substrates, can give coated surfaces having nonstickiness and a low coefficient of friction and excellent in gloss, wear resistance, weather resistance and heat resistance. Thus, it is suited for use in coating rolls and cooking utensils and impregnating processing of glass cloths.

The above-mentioned aqueous TFE polymer dispersion or the above-mentioned TFE polymer fine powder is also preferably used as a processing aid. In a case of use thereof as a processing aid, the aqueous dispersion or fine powder mentioned above is admixed with a host polymer, for instance, whereby the host polymer is improved in melt strength on the occasion of melt processing thereof and/or the resulting polymer composition obtained may show improvements in mechanical strength, electrical characteristics, flame retardancy, anti-dripping performance and sliding property.

The above-mentioned aqueous TFE polymer dispersion or TFE polymer fine powder is also preferably used as a binder for cells or batteries.

The aqueous TFE polymer dispersion or TFE polymer fine powder mentioned above is also preferably used as the processing aid in the form of a composite material together with a resin other than the TFE polymer. The aqueous TFE polymer dispersion or TFE polymer fine powder is suited for use as a raw material for the production of those PTFEs which are described in Japanese Kokai Publications H11-49912 and 2003-24693, U.S. Pat. No. 5,804,654 and Japanese Kokai Publications H11-29679 and 2003-2980. The processing aid comprising the above-mentioned aqueous dispersion or fine powder is not inferior at all to the processing aids described in the respective publications cited above.

The aqueous TFE polymer dispersion mentioned above is also preferably processed by admixing the same with an aqueous dispersion of a melt-processable fluoropolymer, followed by coagulation, to give a co-coagulated powder. This co-coagulated powder is suited for use as a processing aid.

As the melt-processable fluoropolymer, there may be mentioned, for example, FEP, PFA, ETFE and EFEP resins. Among them, FEPs are preferred.

The fluorine-free resin to which the above co-coagulated powder is to be added may be in the form of a powder or pellets or an emulsion. The addition is preferably carried out under shearing force application by such a known method as extrusion kneading or roll kneading from the viewpoint of sufficient mixing up of the respective resins.

The aqueous TFE polymer dispersion mentioned above is also preferably used as a dust-control treatment agent. This dust-control treatment agent can be used in the method of inhibiting a dust-emitting substance from emitting dust by admixing the aqueous dispersion with the dust-emitting substance and subjecting the resulting mixture to compression-shearing action at a temperature of 20 to 200° C. to thereby fibrillate the TFE polymer, for example in carrying out the method described in Japanese Patent No. 2827152 or Japanese Patent No. 2538783. The above-mentioned aqueous TFE polymer dispersion can be suitably used in a dust-control treatment composition, for example the one described in WO 2007/004250 and can also be suitably used in carrying out the dust control treatment method described in WO 2007/000812.

The dust-control treatment agent mentioned above is suitably used in dust control treatment in the fields of building and construction, soil stabilizers, solidifying agents, fertilizers, landfill of incineration ash and hazardous substances, explosion protection, cosmetics and so forth.

The aqueous TFE polymer dispersion mentioned above is also suitably used as a raw material for obtaining a TFE polymer fiber by a dispersion spinning method. The dispersion spinning method is a method of obtaining TFE polymer fibers by admixing the aqueous TFE polymer dispersion with an aqueous dispersion of a matrix polymer, subjecting the resulting mixture to extrusion processing to form an intermediate fibrous structure and baking the intermediate fibrous structure to thereby cause decomposition of the matrix polymer and sintering of TFE polymer particles.

It is also possible to produce high-molecular-weight PTFE using the fluoroethercarboxylic acid mentioned above. The high-molecular-weight PTFE powder obtained by emulsion polymerization is also useful as a raw material for producing a porous PTFE article (membrane). For example, a porous PTFE article (membrane) can be obtained by subjecting the high-molecular-weight PTFE powder to paste extrusion, followed by rolling, and stretching the rolled intermediate product in a non-baked or half-baked condition in at least one direction (preferably stretching it by rolling in the direction of rolling, followed by stretching on a tenter in the width direction). Stretching makes the PTFE easy to fibrillate and give a porous PTFE article (membrane) consisting of knots and fibers.

This porous PTFE article (membrane) is useful as a filter for various purposes and can be suitably used as a filter for liquid chemicals and as an air filter medium, in particular.

It is also possible to produce low-molecular-weight PTFE using the fluoroethercarboxylic acid mentioned above. The low-molecular-weight PTFE may be produced by polymerization or by reducing the molecular weight of high-molecular-weight PTFE obtained by polymerization by an appropriate method known in the art (e.g. thermal degradation, degradation by radiation irradiation).

Low-molecular-weight PTFE species having a molecular weight of 600,000 or below (also called PTFE micropowders) are excellent in chemical stability and very low in surface energy and, in addition, hardly fibrillate and, therefore, are suited for use as an additive for achieving improvements in lubricant property and/or in coat surface texture in manufacturing plastic products, inks, cosmetics, coatings, greases, office automation equipment members, toners and so forth (cf. e.g. Japanese Kokai Publication H10-147617).

The low-molecular-weight PTFE may also be obtained by dispersing a polymerization initiator and the above-mentioned fluoroethercarboxylic acid as an emulsifier in an aqueous medium in the further presence of a chain transfer agent and polymerizing TFE or TFE and a monomer(s) copolymerizable therewith in the resulting medium.

In cases where the low-molecular-weight PTFE obtained by emulsion polymerization is to be used in the form of a powder, the aqueous dispersion mentioned above, when subjected to coagulation, can give powder particles.

Unbaked tapes (unsintered tapes) can also be obtained from the fine PTFE powder obtained by using the fluoroethercarboxylic acid mentioned above.

The fluoroethercarboxylic acid production method of the invention may be the one comprising a step of recovering and purifying a fluoroethercarboxylic acid represented by the general formula (I):

$$Rf^1OCHFCF_2ORf^2COOM \qquad (I)$$

wherein $Rf^1$, $Rf^2$ and M are as defined above, from waste water generated in the step of the coagulation mentioned above or upon washing and/or from an off-gas generated in the step of drying. Such method of producing a regenerated fluoroethercarboxylic acid also constitutes an aspect of the present invention. A method of the recovery and purification mentioned above are not particularly restricted but the recovery and purification can be carried out in the conventional manner.

(II) Melt-Processible Resin (1) In the production method for a fluoropolymer of the invention, the polymerization for producing FEPs is preferably carried out at a polymerization temperature of 60 to 100° C. and a polymerization pressure of 0.7 to 4.5 MPa.

The monomer composition (on the % by mass basis) of the FEPS is preferably TFE:HFP=(60 to 95):(5 to 40), more preferably (85 to 90):(10 to 15). The FEPs may be ones modified with a perfluoro (alkyl vinyl ether) as a third component used in a proportion within the range of 0.5 to 2% by mass relative to the sum of the monomers.

In the above-mentioned FEP production by polymerization, the fluoroethercarboxylic acid mentioned above can be used in the same usage range as in the fluoropolymer production method of the invention; generally, the fluoroethercarboxylic acid is added in an amount of 0.0001 to 2% by mass relative to 100% by mass of the aqueous medium.

In the above-mentioned FEP production by polymerization, such a chain transfer agent as cyclohexane, methanol, ethanol, carbon tetrachloride, chloroform, methylene chloride or methyl chloride is preferably used, and such a pH buffering agent as ammonium carbonate or disodium hydrogenphosphate is preferably used.

(2) In the production method for a fluoropolymer of the invention, the polymerization for producing a TFE/perfluoro (alkyl vinyl ether) copolymer, such as PFA and MFA copolymers, is preferably carried out generally at a polymerization temperature of 60 to 100° C. and a polymerization pressure of 0.7 to 2.5 MPaG.

Preferred as the monomer composition (in mole percent) for the TFE/perfluoro(alkyl vinyl ether) copolymer is TFE:(perfluoro alkyl vinyl ether)=(95 to 99.7):(0.3 to 5), more preferably (97 to 99):(1 to 3). Preferably used as the perfluoro (alkyl vinyl ether)s are those represented by the formula: $CF_2=CFORf^4$ (in which $Rf^4$ is a perfluoroalkyl group containing 1 to 6 carbon atoms).

In the above-mentioned TFE/perfluoro(alkyl vinyl ether) copolymer production by polymerization, the fluoroethercarboxylic acid mentioned above can be used in the same usage range as in the fluoropolymer production method of the invention; generally, the fluoroethercarboxylic acid is added preferably in an amount of 0.0001 to 10% by mass relative to 100% by mass of the aqueous medium.

In the above-mentioned TFE/perfluoro(alkyl vinyl ether) copolymer production by polymerization, such a chain transfer agent as cyclohexane, methanol, ethanol, carbon tetrachloride, chloroform, methylene chloride, methyl chloride, methane or ethane is preferably used, and such a pH buffering agent as ammonium carbonate or disodium hydrogenphosphate is preferably used.

(3) In the production method for a fluoropolymer of the invention, the polymerization for producing the ETFE copolymer is preferably carried out at a polymerization temperature of 20 to 100° C. and a polymerization pressure of 0.5 to 0.8 MPaG.

Preferred as the monomer composition (in mole percent) of the ETFE is TFE:ethylene=(50 to 99):(50 to 1). The ETFE may be those modified with a third monomer in a proportion within the range of 0 to 20% by mass relative to the sum of the monomers. The ratio is preferably TFE:ethylene:third monomer=(63 to 94):(27 to 2):(4 to 10). Preferred as the third monomer are perfluoro(butylethlene), 2,3,3,4,4,5,5-heptafluoro-2-pentene ($CH_2=CFCF_2CF_2CF_2H$) and 2-trifluoromethyl-3,3,3-trifluoropropene (($CF_3)_2C=CH_2$).

In the ETFE production by polymerization, the fluoroethercarboxylic acid mentioned above can be used in the same usage range as in the fluoropolymer production method of the invention; generally, the fluoroethercarboxylic acid is added in an amount of 0.0001 to 2% by mass relative to 100% by mass of the aqueous medium.

In the ETFE production by polymerization, such a chain transfer agent as cyclohexane, methanol, ethanol, carbon tetrachloride, chloroform, methylene chloride or methyl chloride is preferably used.

(4) By utilizing the fluoropolymer production method of the invention, it is also possible to produce an electrolyte polymer precursor. The electrolyte polymer precursor production by polymerization according to the fluoropolymer production method of the invention is preferably carried out at a polymerization temperature of 20 to 100° C. and a polymerization pressure of 0.3 to 2.0 MPaG. The electrolyte polymer precursor is a precursor which comprises such a vinyl ether monomer as specified below and is capable of being converted to an ion-exchanging polymer via a hydrolysis treatment step.

As the vinyl ether monomer to be used in the electrolyte polymer precursor, there may be mentioned fluorinated monomers represented by the formula:

wherein $Y^1$ represents fluorine atom, chlorine atom or a perfluoroalkyl group, n represents an integer of 0 to 3 and the n $Y^1$ moieties may be the same or different, $Y^2$ represents fluorine or chlorine atom, m represents an integer of 1 to 5 and the m $Y^2$ moieties may be the same or different, and A represents $—SO_2X^1$ and/or $—COZ^1$ in which $X^1$ represents a halogen atom and $Z^1$ represents an alkoxyl group containing 1 to 4 carbon atoms. The electrolyte polymer precursor preferably has a monomer composition (mole percent) of TFE:vinyl ether=(50 to 93):(50 to 7).

The above-mentioned electrolyte polymer precursor may be the one modified with a third monomer used in an amount within the range of 0 to 20% by mass of all the monomers.

As the third monomer, there may be mentioned CTFE, vinylidene fluoride, perfluoro(alkyl vinyl ether) species, and divinylbenzene and other polyfunctional monomers.

The thus-obtained electrolyte polymer precursor is molded into a membrane-like shape, for instance, and then subjected to hydrolysis with an alkali solution and to mineral acid treatment for use as a polymer electrolyte membrane in fuel cells, among others.

The melt-processible resin obtained by the method mentioned above is also preferably used as a raw material for obtaining melt-processible resin fibers by the expansion spinning. The expansion spinning is a method of obtaining melt-processible resin fibers by melt-spinning of a melt-processible resin, followed by cooling for solidification, to obtain undrawn yarns and then causing the undrawn yarns to run through a heated cylindrical body for drawing thereof.

The above-mentioned aqueous melt-processible resin dispersion or melt-processible resin is also preferably used as a binder for electric cells or batteries.

(III) Elastomeric Polymer

In carrying out the polymerization for producing a elastomeric polymer according to the method for producing the fluoropolymer of the invention, a pressure-resistant reaction vessel equipped with a stirrer is charged with pure water and the fluoroethercarboxylic acid of the invention and, after deoxygenation, further charged with the monomers, the temperature is raised to a predetermined level, and a polymerization initiator is added to initiate the reaction. Since otherwise the pressure lowers with the progress of the reaction, additional quantities of the monomers are fed to the reaction vessel continuously or intermittently so as to maintain the initial pressure. After completion of feeding of predetermined amounts of the monomers, the feeding is stopped, the monomers remaining in the reaction vessel are purged away, and the temperature is returned to room temperature. The reaction is thus finished. In the case of emulsion polymerization, the polymer latex formed is preferably taken out of the reaction vessel continuously.

In particular when a thermoplastic elastomer is to be produced, it is also possible to employ the method of accelerating the eventual rate of polymerization as compared with the conventional polymerizations by synthesizing fine fluoropolymer particles once at high concentration and, after dilution, further carrying out the polymerization, as disclosed in International Publication WO 00/01741.

In producing the elastomeric polymer, the reaction conditions are to be properly selected from the viewpoint of the desired physical properties of the polymer and of the polymerization rate control. Generally, the polymerization is carried out at a polymerization temperature of −20 to 200° C., preferably 5 to 150° C., and a polymerization pressure of 0.5 to 10 MPaG, preferably 1 to 7 MPaG. Preferably, the pH of the polymerization medium is maintained generally at 2.5 to 9 with a pH adjusting agent, which is to be described later herein, in the conventional manner, for instance.

As the monomer or monomers to be used in producing the elastomeric polymers, there may be mentioned vinylidene fluoride as well as fluorine-containing, ethylenically unsaturated monomers containing at least the same number of fluorine atoms as the number of carbon atoms and capable of copolymerizing with vinylidene fluoride.

As the fluorine-containing ethylenically unsaturated monomers, there may be mentioned, among others, trifluoropropene, pentafluoropropene, hexafluorobutene and octafluorobutene. Among them, hexafluoropropene is particularly suited for use in view of the characteristics of the elastomers obtainable when it blocks the polymer crystal growth. As the fluorine-containing, ethylenically unsaturated monomers, there may further be mentioned trifluoroethylene, TFE, CTFE, etc., and fluorine-containing monomers having one or more chlorine and/or bromine substituents may also be used. Perfluoro(alkyl vinyl ether) species, for example perfluoro (methyl vinyl ether), can also be used. TFE and HFP are preferred for the production of the elastomeric polymer.

The elastomeric polymer preferably has a monomer composition (in % by mass) of vinylidene fluoride:HFP:TFE= (20-70):(30-48):(0-32). The elastomeric polymer the composition of which is within this range shows good elastomer characteristics, chemical resistance and thermal stability.

In the above-mentioned elastomeric polymer production by polymerization, the fluoroethercarboxylic acid mentioned above can be used in the same usage range as in the fluoropolymer production method of the invention; generally, the fluoroethercarboxylic acid is added in an amount of 0.0001 to 2% by mass relative to 100% by mass of the aqueous medium.

In the polymerization of the elastomeric polymer, any of inorganic radical polymerization initiators known in the art can be used as the polymerization initiator. Those water-soluble inorganic peroxides known in the art, for example sodium, potassium and ammonium persulfate, perphosphate, perborate, percarbonate and permanganate, are particularly useful as the inorganic radical polymerization initiator. The radical polymerization initiator can be further activated by a reducing agent such as sodium, potassium or ammonium sulfite, bisulfite, metabisulfite, hyposulfite, thiosulfate, phosphite or hypophosphite, or by a readily oxidizable metal compound such as a ferrous salt, cuprous salt or silver salt. Ammonium persulfate is a suitable inorganic radical polymerization initiator, and the combined use of ammonium persulfate and sodium bisulfite in a redox system is more preferred.

The level of addition of the polymerization initiator is to be properly selected according to a desired molecular weight of the fluoropolymer and the rate of the polymerization reaction; generally, it is set at 0.0001 to 10% by mass, preferably 0.01 to 5% by mass, relative to 100% by mass of the total monomer amount.

In the polymerization of the above elastomeric polymers, any of the chain transfer agents known in the art can be used. In the case of PVDF polymerization, hydrocarbons, esters, ethers, alcohols, ketones, chlorine compounds, carbonates or the like can be used and, in the case of the thermoplastic elastomer, hydrocarbons, esters, ethers, alcohols, chlorine compounds, iodine compounds or the like can be used. Among them, acetone and isopropyl alcohol are preferred in the case of PVDF polymerization and, in the case of thermoplastic elastomer polymerization, isopentane, diethyl malonate and ethyl acetate are preferred from the viewpoint that the rate of reaction is hardly lowered thereby, and $I(CF_2)_4I$, $I(CF_2)_6I$, $ICH_2I$ and like diiodide compounds are preferred from the viewpoint that the polymer termini can be iodinated and the polymer can be used as a reactive one.

The chain transfer agent is used generally in an amount of $0.5 \times 10^{-3}$ to $5 \times 10^{-3}$ mole percent, preferably $1.0 \times 10^{-3}$ to $3.5 \times 10^{-3}$ mole percent.

In the polymerization of the elastomeric polymer, the polymerization of PVDF can be preferably carried out using a paraffin wax or the like as an emulsion stabilizer, and the polymerization of the thermoplastic elastomers can be preferably carried out using a phosphate salt, sodium hydroxide, potassium hydroxide or the like as a pH adjusting agent.

At the time when the polymerization is complete, the elastomeric polymer obtained by the fluoropolymer production method of the invention has an average particle diameter of 0.03 to 1 µm, preferably 0.05 to 0.5 µm and a number average molecular weight of 1,000 to 2,000,000; the solid concentration is 10 to 40% by mass.

The elastomeric polymer obtained by the production method for the fluoropolymer of the invention can be converted, according to need, to dispersions suited for rubber molding processing by adding a dispersion stabilizer such as a hydrocarbon-derived surfactant, and concentrating, for instance. The dispersions are treated by pH adjustment, coagulation, heating, etc. The respective treatments are carried out in the following manner.

The pH adjustment consisting in adjusting the pH to 2 or below by adding a mineral acid such as nitric acid, sulfuric acid, hydrochloric acid or phosphoric acid and/or a carboxylic acid containing not more than 5 carbon atoms and having a pK=4.2 or below, for instance.

The coagulation is carried out by adding an alkaline earth metal salt. As the alkaline earth metal salt, there may be mentioned calcium or magnesium nitrate, chlorate and acetate.

Either of the pH adjustment and the coagulation may be carried out first. Preferably, however, the pH adjustment is carried out first.

After both procedures, the elastomers are washed with an equal volume of water to remove the buffer solution, salt and other impurities occurring in slight amounts within the elastomers, followed by drying. The drying is generally carried out in a drying oven at elevated temperatures of about 70 to 200° C. under circulating hot air.

The concentration of the fluoropolymer mentioned above in the aqueous dispersion obtained by carrying out the polymerization mentioned above is generally 10 to 50% by mass. A preferred lower limit to the fluoropolymer concentration in the above-mentioned aqueous dispersion is 10% by mass, a more preferred lower limit thereto is 15% by mass, a preferred upper limit thereto is 40% by mass, a more preferred upper limit thereto is 35% by mass and a still more preferred upper limit thereto is 30% by mass.

The aqueous dispersion obtained by carrying out the polymerization mentioned above may be concentrated or treated for dispersion stabilization to give a dispersion or may be subjected to coagulation or flocculation, followed by recovery and drying, to give a powder or a solid in some other form.

The fluoroethercarboxylic acid mentioned above can also be suitably used as a dispersant for dispersing a fluoropolymer obtained by polymerization in an aqueous medium.

A aqueous dispersion of the invention comprises fluoropolymer particles, the fluoroethercarboxylic acid mentioned above and an aqueous medium. The aqueous dispersion is the one obtained by dispersing the fluoropolymer particles in the aqueous medium in the presence of the fluoroethercarboxylic acid.

Preferably, the fluoroethercarboxylic acid is contained in the aqueous dispersion of the invention at a concentration of 0.0001 to 15% by mass. At concentration levels below 0.0001% by mass, the dispersion stability may be poor in certain instances and, at levels exceeding 15% by mass, the dispersing effect is impractically no longer proportional to the addition level. A more preferred lower limit to the concentration of the fluoroethercarboxylic acid is 0.001% by mass, a more preferred upper limit thereto is 10% by mass and a still more preferred upper limit thereto is 2% by mass.

A aqueous dispersion of the invention may be an aqueous dispersion obtained by carrying out the polymerization mentioned above, a dispersion obtained by concentration or dispersion stabilization treatment of this aqueous dispersion, or a dispersion obtained by dispersing a fluoropolymer powder in an aqueous medium in a presence of the fluoroethercarboxylic acid mentioned above.

According to the aqueous dispersion production method of the invention, a purified aqueous dispersion can be produced via a step (A) of bringing the aqueous dispersion obtained by the above polymerization into contact with an anion exchange resin in a presence of a nonionic surfactant and a step (B) of concentrating the aqueous dispersion obtained in the step (A) to a solid matter concentration of 30 to 70% by mass relative to 100% by mass of the aqueous dispersion. Such purified aqueous dispersion also constitutes an aspect of the present invention. The nonionic surfactant is not particularly restricted but includes those enumerated hereinabove. The anion exchange resin is not particularly restricted but may be any one known in the art. The method of bringing the dispersion into contact with the anion exchange resin may be any one known in the art.

The method of concentration may be any one known in the art, for example the technique of phase separation, electrical concentration or ultrafiltration. In the above concentration step, the fluoropolymer concentration can be increased to 30 to 70% by mass according to a intended use. Upon concentration, a stability of the dispersion may be reduced in certain cases; in such cases, a dispersion stabilizer may further be added. The above-mentioned fluoroethercarboxylic acid or any of other various surfactants may be added as the dispersion stabilizer. The various dispersion stabilizers include, but are not limited to, nonionic surfactants such as polyoxyalkyl ethers, in particular polyoxyethylene alkylphenyl ethers (e.g. Rohm and Haas' Triton X-100 (trade name)), polyoxyethylene isotridecyl ethers (e.g. Daiichi Kogyo Seiyaku's Noigen TDS80C (trade name), Lion Corporation's Leocol TD90D (trade name), Clariant's Genapol X080 (trade name)) and polyoxyethylene ethers, among others.

The total amount of the dispersion stabilizer(s) is at a level corresponding to a concentration of 0.5 to 20% by mass based on the solid matter in the above-mentioned dispersion. At levels lower than 0.5% by mass, the dispersion stability may be poor in certain instances and, at levels exceeding 20% by mass, the dispersing effect is impractically no longer proportional to the addition level. A more preferred lower level to the level of addition of the dispersion stabilizer is 2% by mass, and a more preferred upper limit thereto is 12% by mass.

The fluoroethercarboxylic acid mentioned above may be removed by the above-mentioned concentration procedure. Since the fluoroethercarboxylic acid is highly soluble in water, it can be removed with higher efficiency as compared with a conventional fluorinated surfactant.

The aqueous dispersion obtained by carrying out the polymerization mentioned above may be subjected, without concentration, to dispersion stabilization treatment to prepare an aqueous dispersion prolonged in pot life and suited for use in certain application. As the dispersion stabilizer to be used, there may be mentioned the same ones as those enumerated hereinabove.

The uses of the aqueous dispersions are not particularly restricted but, when it is applied as the aqueous dispersion as it is, the following uses may be mentioned among others: coating of a substrate which comprises applying it to the substrate and drying the coatings, if necessary followed by baking; impregnation of nonwoven fabrics, resin moldings and other porous supports which comprises impregnating the supports with the dispersion, followed by drying, if necessary further followed by baking; and cast film formation which comprises applying the dispersion onto a substrate such as a glass substrate, drying the coated substrate and, if necessary after immersion in water, peeling off the coatings from the substrate to give a thin film or membrane. In these applications, the dispersion is used as an aqueous dispersion type coating composition, an electrode binder, or a water repellent composition for electrodes, for instance.

The aqueous dispersion of the invention can be used as an aqueous coating composition after incorporation of one or more known formulating ingredients selected from among pigments, thickening agents, dispersing agents, antifoaming agents, antifreezing agents, film-forming auxiliaries and the like and/or further compounding of another polymeric compound.

The invention is also a method of regenerated fluoroethercarboxylic acid production wherein its comprising the step of recovering and purifying a fluoroethercarboxylic acid represented by the general formula (I):

$$Rf^1OCHFCF_2ORf^2COOM \qquad (I)$$

wherein $Rf^1$, $Rf^2$ and M are as defined above, from at least one source selected from among the wastewater generated in the above-described coagulation step, the wastewater generated in the above-mentioned washing step and/or the off-gas generated in the above-mentioned drying step. A method of the above-mentioned recovery and purification are not particularly restricted but the recovery and purification can be carried out by the methods known in the art.

The methods of recovering and purifying the fluoroethercarboxylic acid from the wastewater generated in the coagulation step, the wastewater generated in the washing step and/or the off-gas generated in the drying step are not particularly restricted but those methods known in the art can be employed. Thus, for example, mention may be made of the methods described in United States Patent Application Publications 2007/15937, 2007/25902 and 2007/27251 and, more specifically, the following methods may be mentioned.

As a method of recovering the fluoroethercarboxylic acid from the wastewater mentioned above, there may be mentioned the method comprising bringing the wastewater into contact with such adsorbent particles as ion exchange resin, active carbon, silica gel, clay or zeolite particles for adsorption of the fluoroethercarboxylic acid thereon, followed by separation of the wastewater from the adsorbent particles. If the adsorbent particles with the fluoroethercarboxylic acid adsorbed thereon are incinerated, the fluoroethercarboxylic acid can be prevented from being released into the environment.

It is also possible to recover the fluoroethercarboxylic acid from the ion exchange resin particles with the fluoroethercarboxylic acid adsorbed thereon by desorption or elution therefrom in the conventional manner. For example, when the ion exchange resin particles are anion exchange resin particles, the fluoroethercarboxylic acid or the salt thereof can be eluted by bringing a mineral acid into contact with the anion exchange resin. Then, a water-soluble organic solvent is added to the eluate obtained, whereupon the mixture generally separates into two phases; the fluoroethercarboxylic acid can be recovered by recovering the fluoroethercarboxylic acid-containing lower phase, followed by neutralization. As the water-soluble organic solvent, there may be mentioned such polar solvents as alcohols, ketones and ethers.

As another method of fluoroethercarboxylic acid recovery from ion exchange resin particles, there may be mentioned a method using an ammonium salt and a water-soluble organic solvent and a method using an alcohol, if desired together with an acid. The latter method forms an ester derivative of the fluoroethercarboxylic acid, which can be separated with ease from the alcohol by distillation.

In cases where the wastewater mentioned above contains fluoropolymer particles and/or some other solid matter, the solid fraction is preferably removed prior to bringing the wastewater into contact with adsorbent particles. As a method of removing the fluoropolymer particles and/or other solid matter, there may be mentioned a method comprising adding an aluminum salt or the like to cause the solid fraction to precipitate, followed by separation of the precipitate from the wastewater, and the electric coagulation method, for instance. Mechanical methods for removal may also be employed; for example, the crossflow filtration, depth filtration method and precoat filtration method may be mentioned.

As a method of recovering the fluoroethercarboxylic acid from the off-gas mentioned above, there may be mentioned a method comprising bringing the off-gas into contact with deionized water, an aqueous alkali solution, a glycol ether solution or a like organic solvent, for instance, and recovering the resulting fluoroethercarboxylic acid-containing scrubber solution. The use of a high-concentration aqueous alkali solution as the aqueous alkali solution makes it possible to recover the scrubber solution in a state in which the fluoroethercarboxylic acid occurs as a separate phase, thus making it easy to recover and reutilize the fluoroethercarboxylic acid. As the alkali compound, there may be mentioned alkali metal hydroxides and quaternary ammonium salts, among others.

The fluoroethercarboxylic acid-containing scrubber solution may also be concentrated using a reverse osmosis membrane or the like. While the concentrated scrubber solution generally contains fluoride ion, it is also possible to facilitate the reuse of the fluoroethercarboxylic acid by adding alumina to the scrubber solution after concentration for removing the fluoride ion. The fluoroethercarboxylic acid may also be recovered by bringing the scrubber solution into contact with adsorbent particles for adsorption of the fluoroethercarboxylic acid, followed by the recovering method mentioned above.

The fluoroethercarboxylic acid recovered by any of the methods mentioned above can be reutilized in fluoropolymer production.

EFFECTS OF THE INVENTION

The fluoroethercarboxylic acid of the invention, which has the constitution described hereinabove, is low in bioaccumulation and excellent in surface activity and therefore can be suitably used as a surfactant in fluoropolymer production, as a dispersant in preparing an aqueous fluoropolymer dispersion composition and further in various other fields of application. The method of producing a fluoropolymer according to the invention, which uses the above-mentioned fluoroethercarboxylic acid as a surfactant, can produce the fluoropolymer with great efficiency.

Further, the fluoropolymer aqueous dispersion of the invention, in which a particle comprising a fluoropolymer is dispersed in an aqueous medium in the presence of the fluoroethercarboxylic acid of the invention or the surfactant of the invention, is excellent in stability and workability, among others.

BEST MODES FOR CARRYING OUT THE INVENTION

The following synthesis examples, working example further illustrate the present invention. These examples are, however, by no means limitative of the scope of the invention.

The following methods were used for the measurements carried out in each example.

Solid matter concentration: The aqueous dispersion obtained was dried at 150° C. for 1 hour and the solid matter concentration was calculated based on the loss in mass.

Standard specific gravity (SSG) The measurement was carried out according to ASTM D 1457-69.

Average primary particle diameter (PTFE): Determined indirectly from the transmittance of the incident light of 550 nm per unit length as transmitted by each dispersion diluted to a solid matter concentration of about 0.02% by mass based on a working curve constructed by plotting such transmittance data against the average particle diameter data obtained from electron photomicrographs.

The transmittance measurements were carried out using a Microtrac 9340 UPA dynamic light scattering measuring apparatus (product of Honeywell).

$^1$H-NMR, $^{19}$F-NMR and $^{13}$C-NMR spectra were measured using Varian's nuclear magnetic resonance spectrometry (NMR) system 400. Tetramethylsilane or $CCl_3F$ was added as an internal standard substance; in $^1$H-NMR (400 Hz), the chemical shift of the signal of tetramethylsilane was regarded as 0 ppm; in $^{19}$F-NMR (376 Hz), the chemical shift of the signal of $CCl_3F$ was regarded as 0 ppm; and, in $^{13}$C-NMR (100 Hz), the chemical shift of the signal of tetramethylsilane was regarded as 0 ppm.

SYNTHESIS EXAMPLE 1

Method of synthesizing
$CF_3OCHFCF_2OCH_2CF_2COONH_4$

Tetrafluorooxetane (45 g) was added dropwise over 1 hour to a suspension of sodium acetate (61.8 g) in ethanol (150 ml) at an inside temperature of 45 to 70° C. After dropping, the mixture was further heated under reflux for 1 hour. The reaction mixture was cooled, the salt formed was filtered off through Celite, the residue on the filter was thoroughly washed with ethanol, concentrated sulfuric acid (4 ml) was added, and the resultant mixture was heated under reflux for 8 hours. The solvent was distilled off under reduced pressure, and ether was added to the residue, followed by washing with water, $NaHCO_3$ and a saturated aqueous solution of sodium chloride. Drying, concentration and distillation under reduced pressure gave 43.1 g (yield: 81.8%) of $HOCH_2CF_2COOEt$.

$HOCH_2CF_2COOEt$ (30 g), tert-BuOK (1.5 g), tert-BuOH (10 g) and a stirrer bar were placed in a 100-ml autoclave equipped with a pressure gage, valve and safety valve, and the autoclave was tightly closed. After several repetitions of replacement of the autoclave inside atmosphere with nitrogen, the pressure was reduced. Then, at room temperature, $CF_3OCF=CF_2$ (PMVE) was fed into the autoclave until arrival of the inside pressure at 0.3 MPa and, thereafter, the contents were stirred with a magnetic stirrer at room temperature. With the progress of the reaction, the pressure fell, so that PMVE was further fed into the autoclave until arrival of the inside pressure at 0.3 MPa. A total of 36 g of PMVE was introduced by repeating such procedure, and the reaction was carried out for 18 hours. Thereafter, the autoclave was opened, the contents were washed with several portions of 10% (by weight) aqueous HCl and several portions of a saturated aqueous solution of sodium chloride, and the organic phase was dried over magnesium sulfate, then filtered and distilled under reduced pressure to give 45.1 g of a mixture of $CF_3OCHFCF_2OCH_2CF_2COOEt$ and $CF_3OCHFCF_2OCH_2CF_2COOH$. The structures of these compounds were identified by $^1$H-NMR, $^{19}$F-NMR and $^{13}$C-NMR.

This mixture was subjected to hydrolysis with a 6 N aqueous solution of sodium hydroxide, and the hydrolysis product was lyophilized and then neutralized with 12 N hydrochloric acid. The thus-obtained $CF_3OCHFCF_2OCH_2CF_2COOH$ was neutralized with aqueous ammonia and the neutralization product was lyophilized to give 45.7 g of $CF_3OCHFCF_2OCH_2CF_2COONH_4$.

Spectral data concerning the thus-obtained $CF_3OCHFCF_2OCH_2CF_2COOEt$ are shown below.

$^1$H-NMR (δ, ppm): 5.90 (dt, 1H), 4.37 (m, 4H), 1.34 (t, 3H)

$^{19}$F-NMR (δ, ppm): −60.45 (d, 3F), −90.40 (d, 1F), −91.02 (d, 1F), −114.28 (t, 2F), −145.63 (d, 1F)

$^{13}$C-NMR (δ, ppm): 163.70 (t), 122.66 (q), 118.97 (td), 113.54 (t), 100.53 (dt), 65.134 (s), 64.36 (tt), 14.18 (s)

Spectral data concerning the $CF_3OCHFCF_2OCH_2CF_2COOH$ obtained are shown below.

$^1$H-NMR (δ, ppm): 11.96 (s, 1H), 5.80 (dt, 1H), 4.43 (t, 2H)

$^{19}$F-NMR (δ, ppm): −60.52 (d, 3F), −90.51 (d, 1F), −91.04 (d, 1F), −114.70 (t, 2F), −145.42 (d, 1F)

$^{13}$C-NMR (δ, ppm): 167.48 (t), 122.93 (q), 119.15 (td), 113.68 (t), 100.66 (dt), 64.16 (tt)

SYNTHESIS EXAMPLE 2

Method of synthesizing
$CF_3CF_2CF_2OCHFCF_2OCH_2CF_2COONH_4$

The $HOCH_2CF_2COOEt$ (30 g) obtained by the method described in Synthesis Example 1, tert-BuOK (1.5 g), tert-BuOH (10 g) and a stirrer bar were placed in a 300-ml four-necked flask equipped with a dropping funnel, cold finger and thermometer. After several repetitions of replacement of the flask inside atmosphere with nitrogen, $CF_3CF_2CF_2OCF=CF_2$ (51.8 g) was added dropwise at 20-25° C. over 5 hours while the flask contents were stirred with the magnetic stirrer. Then, after overnight stirring, the flask contents were washed with several portions of a 10% (by weight) aqueous solution of HCl and several portions of a saturated aqueous solution of sodium chloride, then dried over magnesium sulfate and filtered, and the filtrate was distilled under reduced pressure to give 62.1 g of a mixture of $CF_3CF_2CF_2OCHFCF_2OCH_2CF_2COOEt$ and $CF_3CF_2CF_2OCHFCF_2OCH_2CF_2COOH$. The structures of these compounds were identified by $^1$H-NMR, $^{19}$F-NMR and $^{13}$C-NMR. This mixture was subjected to hydrolysis with a 6 N aqueous solution of sodium hydroxide, the hydrolysis product was lyophilized and then neutralized with 12 N hydrochloric acid, and the thus-obtained $CF_3CF_2CF_2OCHFCF_2OCH_2CF_2COOH$ was neutralized with aqueous ammonia and the neutralization product was lyophilized to give 47.3 g of $CF_3CF_2CF_2OCHFCF_2OCH_2CF_2COONH_4$.

Spectral data concerning the thus-obtained $CF_3CF_2CF_2OCHFCF_2OCH_2CF_2COOEt$ are shown below.

$^1$H-NMR (δ, ppm): 6.05 (dt, 1H), 4.35 (m, 4H), 1.33 (t, 3H)

$^{19}$F-NMR (δ, ppm): −81.76 (t, 3F), −85.14 (d, 1F), −87.07 (d, 1F), −90.51 (d, 1F), −91.56 (d, 1F), −114.41 (t, 2F), −129.95 (s, 2F), −144.03 (d, 1F)

$^{13}$C-NMR (δ, ppm): 163.42 (t), 119.07 (qt), 119.06 (td), 117.65 (tt), 113.47 (t), 108.59 (tqt), 99.58 (dt), 64.86 (s), 64.36 (tt), 14.19 (s)

Spectral data concerning the $CF_3CF_2CF_2OCHFCF_2OCH_2CF_2COOH$ obtained are shown below.

$^1$H-NMR (δ, ppm): 11.79 (s, 1H), 5.97 (dt, 1H), 4.40 (t, 2H)

$^{19}$F-NMR (δ, ppm): −81.68 (t, 3F), −85.05 (d, 1F), −87.22 (d, 1F), −90.53 (d, 1F), −91.40 (d, 1F), −114.78 (t, 2F), −129.86 (s, 2F), −144.86 (d, 1F)

$^{13}$C-NMR (δ, ppm): 168.49 (t), 119.26 (qt), 119.23 (td), 117.87 (tt), 113.61 (t), 108.81 (tqt), 99.67 (dt), 64.23 (tt)

Example 1

PTFE Latex Preparation

A 3-liter stainless steel autoclave equipped with a agitation blade was charged with 1.5 L of deionized water, 60 g of paraffin wax (melting point 60° C.) and 1.5 of $CF_3OCHFCF_2OCH_2CF_2COONH_4$, and the system inside atmosphere was replaced with tetrafluoroethylene [TFE]. The inside temperature was raised to 70° C., TFE was fed into the autoclave until arrival of the inside pressure at 0.78 MPa, and 3.75 g of a 1% (by mass) aqueous solution of ammonium persulfate [APS] was further fed to initiate the reaction. To prevent the polymerization system inside pressure from falling with the progress of the polymerization, TFE was continuously supplemented to maintain the inside pressure at 0.78 MPa, and the reaction was continued in this manner. At 6.5 hours after the start of the polymerization, the polymerization was terminated by purging the residual TFE.

The solid matter concentration of this aqueous dispersion was 29.2% by mass, the standard specific gravity was 2.200, and the average primary fluoropolymer particle diameter was 282 nm.

INDUSTRIAL APPLICABILITY

The fluoroethercarboxylic acid of the invention can be utilized as a surfactant in fluoropolymer production and as a dispersant for use in aqueous fluoropolymer dispersion compositions.

The invention claimed is:

1. A fluoroethercarboxylic acid which is represented by the general formula (I):

$$Rf^1OCHFCF_2ORf^2COOM \quad (I)$$

wherein $Rf^1$ represents a partially or fully fluorinated alkyl group, which is optionally interrupted with one or more oxygen atoms, $Rf^2$ represents a partially or fully fluorinated alkylene group, which is optionally interrupted with one or more oxygen atoms, and M represents a monovalent alkali metal, $NH_4$ or H.

2. The fluoroethercarboxylic acid according to claim 1, wherein $Rf^2$ is —$CH_2CF_2$—.

3. The fluoroethercarboxylic acid according to claim 1, wherein $Rf^1$ is $CF_3(CF_2)_n$—, wherein n represents an integer of 0 to 2.

4. A production method of the fluoroethercarboxylic acid according to claim 1,
which comprises the addition reaction step of allowing a hydroxyalkanoic acid derivative represented by the general formula (1):

$$HOCH_2CF_2COOR \quad (1)$$

wherein R represents an alkyl group or H, to add to a fluoro(vinyl ether) represented by the general formula (2):

$$CF_2\!=\!CFORf^1 \quad (2)$$

wherein $Rf^1$ is as defined above, in the presence of an alkali compound.

5. The production method according to claim 4, wherein the alkali compound is an alcoholate.

6. The production method according to claim 5, wherein the addition reaction step is carried out in the simultaneous presence of an alcoholate and an alcohol corresponding to the alcoholate.

7. The production method according to claim 4, which further comprises the step of preparing the hydroxyalkanoic acid represented by the general formula (1) by causing the ring opening of tetrafluorooxetane.

8. A production method of a fluoroethercarboxylic acid which comprises the step of bringing the fluoroethercarboxylic acid according to claim 1, into contact with fluorine to give said fluoroethercarboxylic acid represented by the general formula (II):

$$Rf^1OCF_2CF_2ORf^2COOM \quad (II)$$

wherein $Rf^1$ represents a partially or fully fluorinated alkyl group, which is optionally interrupted with one or more oxygen atoms, $Rf^2$ represents a partially or fully fluorinated alkylene group, which is optionally interrupted with one or more oxygen atoms, and M represents a monovalent alkali metal, $NH_4$ or H.

9. A surfactant
which comprises the fluoroethercarboxylic acid according to claim 1.

10. A surfactant for polymerization
which comprises the fluoroethercarboxylic acid according to claim 1.

11. A production method of a fluoropolymer,
which comprise the step of polymerizing a fluoromonomer or fluoromonomers in an aqueous medium containing the fluoroethercarboxylic acid according to claim 1.

12. The production method of the fluoropolymer according to claim 11,
wherein the content of the fluoroethercarboxylic acid is 0.0001 to 10% by mass relative to 100% by mass of the aqueous medium.

13. An aqueous fluoropolymer-containing dispersion containing the fluoroethercarboxylic acid according to claim 1,
wherein the fluoropolymer has an average particle diameter of 50 to 500 nm.

14. A production method of a purified aqueous dispersion production,
which comprises the step (A) of bringing the aqueous dispersion according to claim 13 into contact with an anion exchange resin in the presence of a nonionic surfactant and the step (B) of concentrating the aqueous dispersion obtained in the step (A) to produce an aqueous dispersion having a solid matter content of 30 to 70% by mass of the aqueous dispersion.

15. A fine powder being produced by coagulating the aqueous dispersion according to claim 13.

16. A production method of a regenerated fluoroethercarboxylic acid, which comprises
the step of recovering a fluoroethercarboxylic acid represented by the general formula (I):

$$Rf^1OCHFCF_2ORf^2COOM \quad (I)$$

wherein $Rf^1$ represents a partially or fully fluorinated alkyl group, which is optionally interrupted with one or more oxygen atoms, $Rf^2$ represents a partially or fully fluorinated alkylene group, which is optionally interrupted with one or more oxygen atoms, and M represents a monovalent alkali metal, $NH_4$ or H
from at least one source selected from among a wastewater generated in the step of coagulation of the aqueous dispersion according to claim 13, a wastewater generated upon washing thereof and/or a off-gas generated in drying thereof, and
the step of purifying the recovered fluoroethercarboxylic acid obtained by said step to produce said regenerated fluoroethercarboxylic acid.

* * * * *